United States Patent [19]
Fried

[11] Patent Number: 5,836,927
[45] Date of Patent: Nov. 17, 1998

[54] DEVICE TO AID IN THE SELF ADMINISTRATION OF EYEDROPS

[76] Inventor: George Fried, 222 Martling Ave., Tarrytown, N.Y. 10591

[21] Appl. No.: 729,700

[22] Filed: Oct. 7, 1996

[51] Int. Cl.$^6$ ................................................ A61U 35/00
[52] U.S. Cl. ........................... 604/300; 604/294; 604/301
[58] Field of Search ..................................... 604/294–303

[56] References Cited

U.S. PATENT DOCUMENTS

| | | |
|---|---|---|
| 4,052,985 | 10/1977 | Coleman et al. ......................... 604/301 |
| 4,183,355 | 1/1980 | Meckler ................................... 604/302 |
| 5,030,214 | 7/1991 | Spector .................................... 604/294 |
| 5,037,406 | 8/1991 | Smith et al. .............................. 604/301 |
| 5,059,188 | 10/1991 | Goddard .................................. 604/300 |
| 5,255,024 | 10/1993 | Jensen ...................................... 604/300 |
| 5,366,448 | 11/1994 | Basilice et al. .......................... 604/300 |
| 5,569,224 | 10/1996 | Michalos .................................. 604/300 |

FOREIGN PATENT DOCUMENTS 0939019  6/1982  U.S.S.R. .

Primary Examiner—Robert A. Clarke
Assistant Examiner—David J. Cho
Attorney, Agent, or Firm—Galgano & Burke

[57] ABSTRACT

An device for administering eyedrops from an eyedrop container to an eye of a user, comprising an eyeglass frame and eyedrop guide wherein the eyedrop guide is attached to the eyeglass frame and is variably adjustable over the user's eye for facilitating dispersement of an eyedrop. A level indicator or alarm is used to determine when the guide or the eyedrop container is ideally positioned for eyedrop administration.

32 Claims, 7 Drawing Sheets

DEVICE TO AID IN THE SELF ADMINISTRATION OF EYEDROPS

The present invention is directed to a Small Business Innovation Research Program, Phase I Grant No. 1 R43 EY11077-01, awarded by the Department of Health and Human Services, Public Health Service, National Institutes of Health. The government has certain rights in the invention.

The present invention relates to eyedrop guides. More particularly, the present invention relates to a novel device which aids in the self-administration of eyedrops.

BACKGROUND

Illnesses of the eye, such as glaucoma, keratoconjunctivitis ("dry eyes"), infections of the eye, and other conditions following post surgery, are generally treated with eyedrops. Many individuals, especially the elderly, have difficulty self-administering eyedrops and a significant amount of medication can be wasted during the effort.

Generally, the self-administering process involves raising an eyedrop container above one's eye, taking aim as best one can over the eye, and squeezing the container a certain number of times (as prescribed) to disperse the eyedrop solution. When taking the proper position for administering the eyedrop solution, some people assume a sitting position while others assume a prone position. Typically after the first drop, which often misses, the person adjusts his/her position to take better aim for the second drop. This results in wasted medication. Moreover, if the user does not realize that the first drop misses or becomes frustrated with repeated misses, the result is inadequate treatment and significant waste of medication. This is often the case with the elderly, an age group especially prone to eye ailments.

Several devices for aiding in the self-administration of eyedrops have been provided in the past. For example, U.S. Pat. Nos. 5,255,024, 4,468,103, 4,183,355, and 3,446,209 all disclose a variety of eyedrop apparatii which are designed to aid in the self administration of eyedrops. These devices have disadvantages.

For example, U.S. Pat. No. 5,255,024 to Jensen and U.S. Pat. Nos. 4,183,355 and 4,468,103 to Meckler all disclose eyeglass frames which have slidably engagable guides positioned in place of the lenses. The guides have one or, in some cases, two slots located therethrough. In these devices, however, movement of the eyedrop container is restricted to movement within the plane of the slides and a patient is restricted from manipulating (i.e. pulling down) his/her eyelid prior to administration. U.S. Pat. No. 3,446,209 to Macha discloses a similar device to the aforementioned patents, however, in this case the eyedrop container can only be positioned at the center of the lense thereby limiting the overall versatility and usefulness of the device.

It would therefore be desirable to provide a device which can overcome disadvantages known in the field and provide a device which allows a patient to accurately aim the eyedrop container over his/her eye and manipulate his/her eye prior to self-administration thus reducing the significant waste inherent with the overall eyedrop self-administration process.

SUMMARY OF THE INVENTION

Various embodiments of the present invention provide a novel device for administering a liquid eyedrop from an eyedrop container to an eye of a user comprising an eyeglass frame with an upper bridge portion and at least one eyedrop guide attached to the eyeglass frame. The eyedrop guide is vertically adjustable in a substantially arcuate fashion, preferably from a position located proximate the lower portion of a patient's eye to a position located near the upper portion of a patient's eye. Advantageously, the eyedrop guide and, in turn, the eyedrop container, is positionable over the conjunctival sac near the center of the arcuate path; the conjunctival sac typically considered the optimum point to administer an eyedrop according to ophthalmologically accepted protocol. The eyedrop container is releasably attached to the eyedrop guide and the eyeglass frame is secured proximate the eye of the patient, e.g. by two ear pieces, a strap or a band.

Accordingly, the present invention provides a device for aiding in the self-administration of eyedrops wherein a patient is free to manually adjust the eyedrop guide to an ideal position over the eye while at the same time manipulate the lower portion of his/her eye prior to administration, thus increasing the accuracy of the overall eyedrop process. Preferably, a generally hollow eyedrop guide is disposed a certain distance from the eye and is movable in a substantially arcuate path above the patient's eye thus allowing a patient to insert his/her finger under the guide (or a portion thereof) to manipulate his/her eye or eyelid prior to administration of the eyedrop.

One embodiment of the present invention provides a device for aiding in the self-administration of eyedrops wherein the guide portion comprises two portions; the first portion is attached to the eyeglass frame and the second portion is both releasably engagable with the first portion and selectively engagable with various eyedrop containers of different shapes and sizes.

Another embodiment of the present invention provides a self-administration eyedrop device which comprises a mechanism which indicates when the dropper or the guide is oriented in the ideal position for dispersing the eyedrop solution. Preferably, the mechanism includes an electronic leveling indicator which signals the patient, e.g. visually or audibly when the eyedrop container is correctly positioned over the eye.

A further embodiment of the present invention provides a device for aiding in the self-administration of eyedrops wherein the eyedrop guide comprises two fixed ports which releasably engage the eyedrop container. One port is used when the patient wishes to accurately administer the eyedrop when oriented in the sitting position and another port is used when the patient wishes to accurately administer the medication when oriented in the prone position.

These and other aspects of the present invention are described in greater detail below.

BRIEF DESCRIPTION OF THE DRAWINGS

In the drawings, wherein similar reference characters denote similar elements throughout the several views.

DETAILED DESCRIPTION

In accordance with one embodiment the present invention, a device for administering a liquid eyedrop from an eyedrop container to an eye of a user comprises an eyeglass frame having an upper bridge portion and at least one eyedrop guide attached to the eyeglass frame. The eyedrop guide is adjustable in a substantially arcuate path between a first position located a fixed distance from the bridge portion to another subsequent position located a closer distance to the bridge portion. An eyedrop container selectively attaches to the eyedrop guide and the eyeglass frame is secured about the head of a patient.

In one particular embodiment, the eyeglass frame additionally comprises an eyeglass shield portion which attaches to the bridge portion and which is sized and dimensioned to substantially cover at least one eye of the patient. In this particular embodiment, the guide portion is attached to the eyeglass shield preferably at the center thereof. Advantageously, the eyeglass shield portion substantially covers both of the patient's eyes and the eyedrop guide is selectively moveable across the eyeglass shield above the patient's eyes. In another embodiment, two eyedrop guides are positioned within the shield, e.g., one substantially positioned over the right eye and the another substantially positioned over the left eye.

Preferably, the eyedrop container is threadably engaged with the eyedrop guide, but in some cases it may be desirable to provide alternate means of releasable. attachment, e.g., snap-fit or frictional engagement. Advantageously, the eyedrop guide, or a portion thereof, can releasably engage different size eyedrop containers or can be easily modified to accommodate the same. For example, in one particular embodiment, it may be desirable to provide a two-piece eyedrop guide wherein a first piece attaches to the eyeglass frame (or shield) and a second piece attaches to both the first piece and different size eyedrop containers. Or, in other cases, it may be desirable to provide, a first piece which is universally standardized to accept a variety of second pieces and second pieces which accept eyedrop containers of many different shapes and sizes.

Most desirably, the eyedrop guide is disposed a certain distance away from the eye and is moveable, or a portion of the guide is moveable, along a substantially arcuate path above the patient's eye. In other cases it may be desirable to selectively position the eyedrop guide (or the moveable portion of the same) at certain fixed positions or intervals along the path to further facilitate the administering process. In one particular embodiment, the eyedrop guide is comprised of two portions, the first portion or base portion is attached to the eyeglass frame (or shield) and the second portion removably attaches to the first portion in a snap-fit manner. In this particular embodiment, the second portion further comprises two resilient flanges each having a notch located therein which releasably engage a guide bar disposed on and along the first portion. The second portion by virtue of the notch and guide bar configuration is free to move along the specified path of the guide bar which is preferably arcuate.

In another embodiment, at least one eyedrop guide comprises at least two fixed ports located over each eye for selectively receiving at least one eyedrop container. This particular embodiment represents a somewhat simpler embodiment wherein the patient is free to orient himself/herself in either of two positions for administering the eyedrop solution, e.g., a sitting position and a prone position. The patient secures an eyedrop container to one of two ports and orients himself/herself so that the eyedrop container is substantially vertical prior to administration. The ports are ideally positioned to receive the container so that the tip of the container is generally centered over the eye for dispersement purposes. Ideally, the receiving ports are also disposed a certain distance away from the eye so as to allow a patient to manipulate his/her eye or eyelid prior to administration.

Preferably, the present invention also comprises a mechanism for determining the ideal position for eyedrop dispersement over a patient's eye. In some cases, this mechanism can comprise a simple leveling device which signals a patient either visually or audibly when the eyedrop container and/or eyedrop guide is oriented in a level position for eyedrop dispersement. In other cases, a more complicated mechanism may be utilized which signals the patient when the eyedrop container is precisely positioned over the ideal portion of the eye or, in some cases, any other predetermined portion of the eye.

In one particular embodiment, a cap is provided to seal the eyedrop container when the eyedrop container is engaged with the eyedrop guide thereby allowing a patient to keep the present invention configured for later or repeated administration. Most desirably, the cap is releasably engagable with the top portion of the eyedrop container in a threadably secured, snap-fit or friction fit manner. In some cases it may be desirable to provide alternate means for securing the same.

Figure 1:
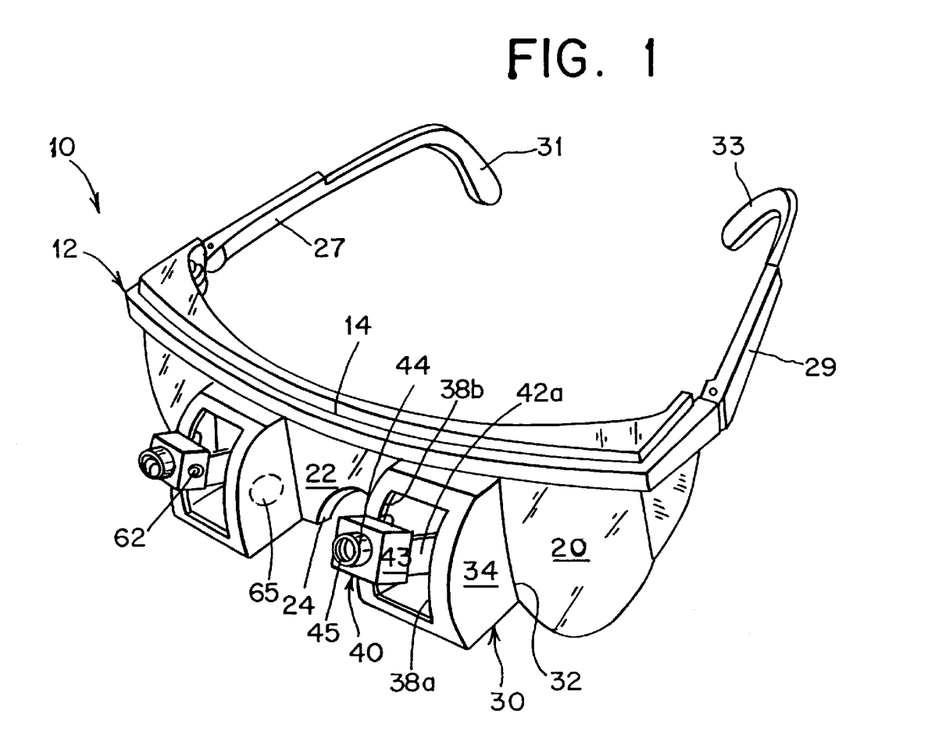
FIG. 1 is a perspective view of one embodiment of the present invention.

Turning now in detail to the drawings, and in particular FIG. 1, therein illustrated is a novel device for aiding in the self-administration of eyedrops according to one embodiment of the present invention generally designated by reference number 10. Device 10 comprises an eyeglass-type frame 12 having a bridge portion 14, two rearwardly extending temple portions 27, 29 extending from opposite sides of bridge 14, a shield portion divided by a nose rest 24 into a left shield 20 and a right shield 22, and at least one eyedrop guide 30. In the particular embodiment of FIG. 1, one eyedrop guide 30 is attached (either fixedly or releasably) to each shield portion 20, 22 generally above a patient's left and right eyes, respectively.

As noted above, temple portions 27 and 29 are preferably attached to the outermost opposite distal ends of bridge portion 14 and extend rearwardly therefrom. Ear pieces 31 and 33 are attached to the end of each temple portion 27, 29, respectively, and depend in a general downward direction around the right and left ears of a patient for securing device 10 on the head of the patient (seen best in FIG. 2). Ear pieces 33 and 31 allow the patient to orient his/her head in various positions for administering purposes without device 10 slipping or falling from its desired position.

Figures 3, 4:
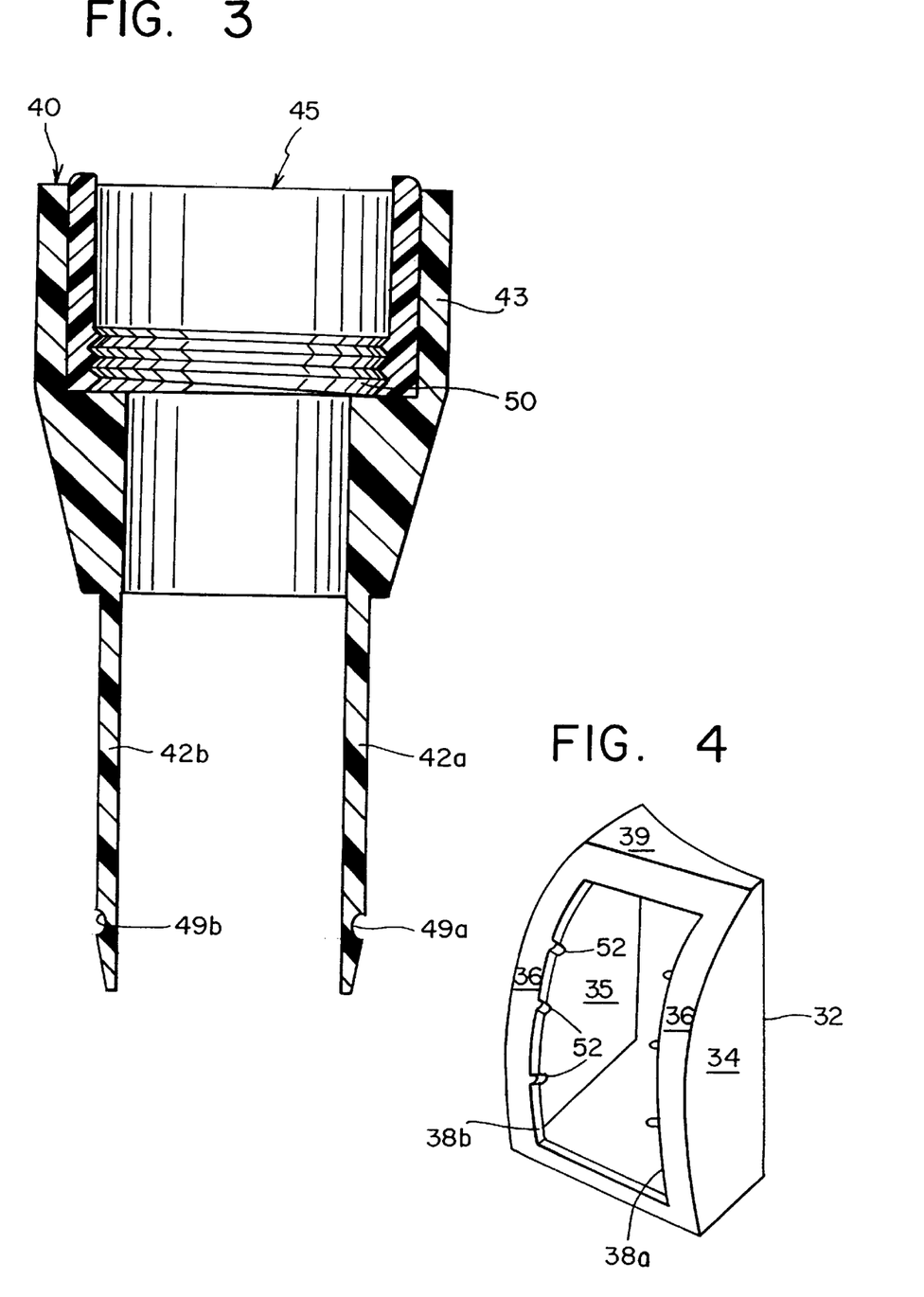
FIG. 3 is an enlarged cross section of one embodiment of a moveable eyedrop container port.
FIG. 4 is a perspective view of one embodiment of an eyedrop guide.

As best shown in FIG. 4, eyedrop guide 30 comprises left and right sidewalls 34 and 35, respectively, and top portion 39 all of which extend from shield 20, 22 and frontal plate 36 which, together, define an inner cavity 37. Sidewalls 34 and 35 are preferably both dimensioned so that their outermost respective edges are curved in a somewhat arc-like manner. Frontal plate 36 is integral with sidewalls 34, 35 outermost edges so that it has a radius of curvature generally in a direction towards bridge 14 as seen best in FIG. 1.

As can be appreciated from the present description, since inner cavity 37 is defined by walls 34, 35 and 39 and frontal plate 36, a lower opening 47 is provided below eyedrop guide 30. Preferably, lower opening 47 is sufficiently dimensioned to allow the finger of a patient access into and under the lower portion of the eyedrop guide 30 in order to manipulate the patient's eyelid (exposing the cunjunctival sac of a patient's eye) prior to administration thereby increasing the odds of successful dispersement of the eyedrop solution.

Although not shown in the accompanying drawings, eyedrop guide or guides 30 can be fixedly or releasably attached to the eyeglass frame 12 or, preferably, to one or both sides of shield 20, 22. Preferably, the rear edge 32, or perhaps another portion of the eyedrop guide 30 is separable from the shield and engages a track located (not shown) within one or both sides of the shield 20, 22. In one particular embodiment, eyedrop guide 30 is slideably mounted on left shield 20 above the left eye of a patient and can be selectively laterally slid across to shield 22 above a patient's right eye. In another embodiment, the eyedrop guide 30 is dimensioned somewhat smaller than represented in FIG. 1 so that the guide 30 can also move vertically along a vertically oriented track located within either one or both of the shields 20, 22 (not shown).

Figure 2:
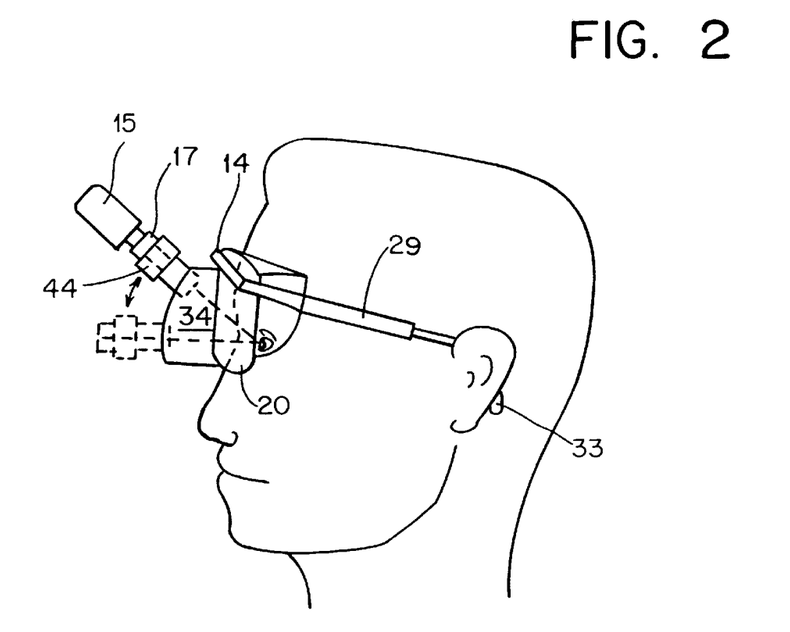
FIG. 2 is a side view of the embodiment shown if FIG. 1 positioned on the patient.

As depicted in FIGS. 1 and 2 and seen best in FIG. 3, eyedrop guide 30 also comprises a moveable container port 40 which is slideably disposed in a generally vertically oriented arcuate channel having vertical sides 38a and 38b formed within frontal plate 36. Container port 40 comprises base portion 43, receiving port 45 and flanges 42a and 42b. Receiving port 45 is formed within base 43 and is generally dimensioned to selectively engage container 15 (see FIG. 2) in a secure manner. Preferably, port 45 threadably secures container 15, but in some cases it may be desirable for container 15 to engage port 45 in a snap-fit or friction-fit manner. Flanges 42a and 42b depend from base portion 43 and are engagable with the outer edges of channel 38a and 38b, respectively, via notches 49a and 49b (see FIG. 3) located within each flange 42a, 42b, respectively. As can be appreciated from the present disclosure, port 45 and, therefore, eyedrop container 15, is moveable along the channel edges 38a, 38b in a substantially arcuate manner above the patient's eye generally from a point beneath the patient's eye to a point closer to the bridge portion 14. In some cases, as best illustrated in FIG. 4, it may be desirable to provide a series of detents 52 located at various fixed positions along the outer edges of channel 38a, 38b so that container port 40 will selectively engage the detents 52 at fixed intervals along the path thereby allowing a patient to repeatably administer the solution at a predetermined position along the arcuate path.

Although the various figures show frontal plate 36 having a radius of curvature generally shaped towards eyeglass shield 20, in some cases it may be desirable to have sidewalls 34, 35 and top portion 39 all extend equally from shield 20 with frontal plate 36 formed flat (i.e., no radius of curvature) and have an arc-like guide bar (not shown) formed within each sidewall 34, 35. Flanges 42a and 42b of container port 40 can engage the arc-like guide bar in a snap-fit, tongue and groove, or friction-fit manner thus allowing the patient to position container 15 above his/her eye.

An indicating mechanism can also be incorporated with device 10 to determining the ideal position for eyedrop dispersement over a patient's eye. This will enable users who do not have the spatial feel or kinesthetic sense to repeatably assume the same position during the administration process. In one particular embodiment, the indicating mechanism can comprise a simple leveling device having a battery 65 attached thereto which will signal a patient via indicator 62 (visual or audible) when the eyedrop container 15 and/or eyedrop guide 30 is oriented in a level position for eyedrop dispersement. In another embodiment, a more complicated mechanism, e.g. a computerized positioning device, may be utilized to signal the patient when the eyedrop container 15 or guide 30 is precisely positioned over any predetermined ideal portion of the eye or, in some cases, any other predetermined portion of the eye.

Figure 10A:
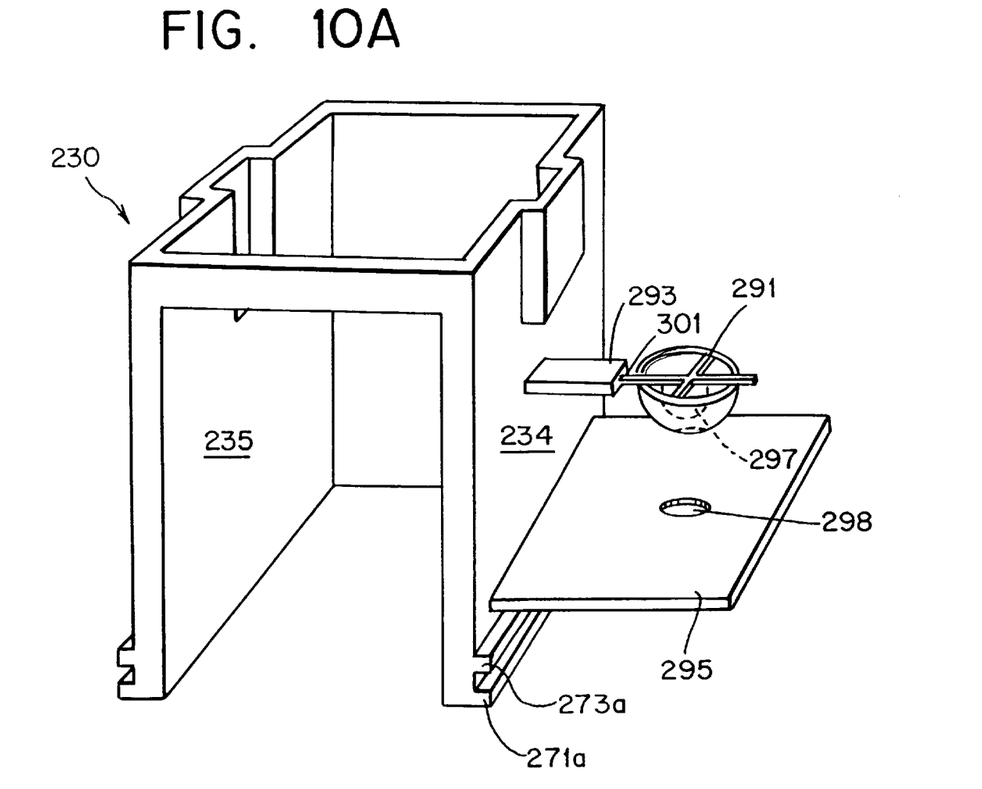
FIG. 10a is a perspective view of an alternative embodiment the eyedrop guide shown with an indicating mechanism.
Figure 10B:
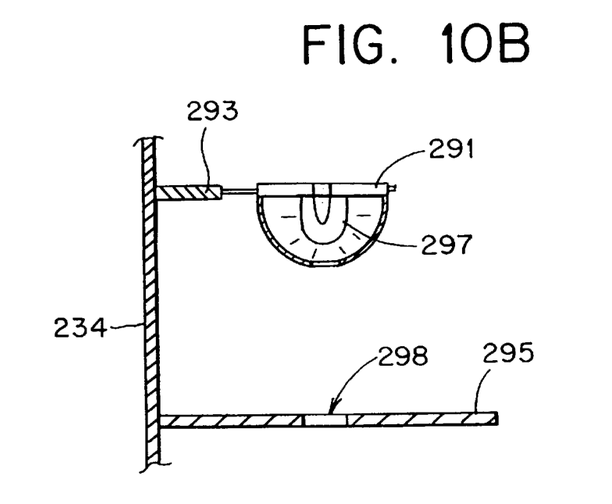
FIG. 10b is a cross section of an indicating mechanism.

As can be appreciated, there are several methods by which an ideal and/or level indication can be achieved. For example, a bubble-type leveling device with an optical bubble sensor or a solid-state leveling device with a built-in mercury drop that makes contact with various wire terminals depending on its position. Both of these level indicators feed their signal into an electronic circuitry which activates the indicator signal 62. Another embodiment of the indicating mechanism, e.g. a gimbal-like device, as depicted in FIG. 10a and 10b, is described hereinbelow.

Figure 5:
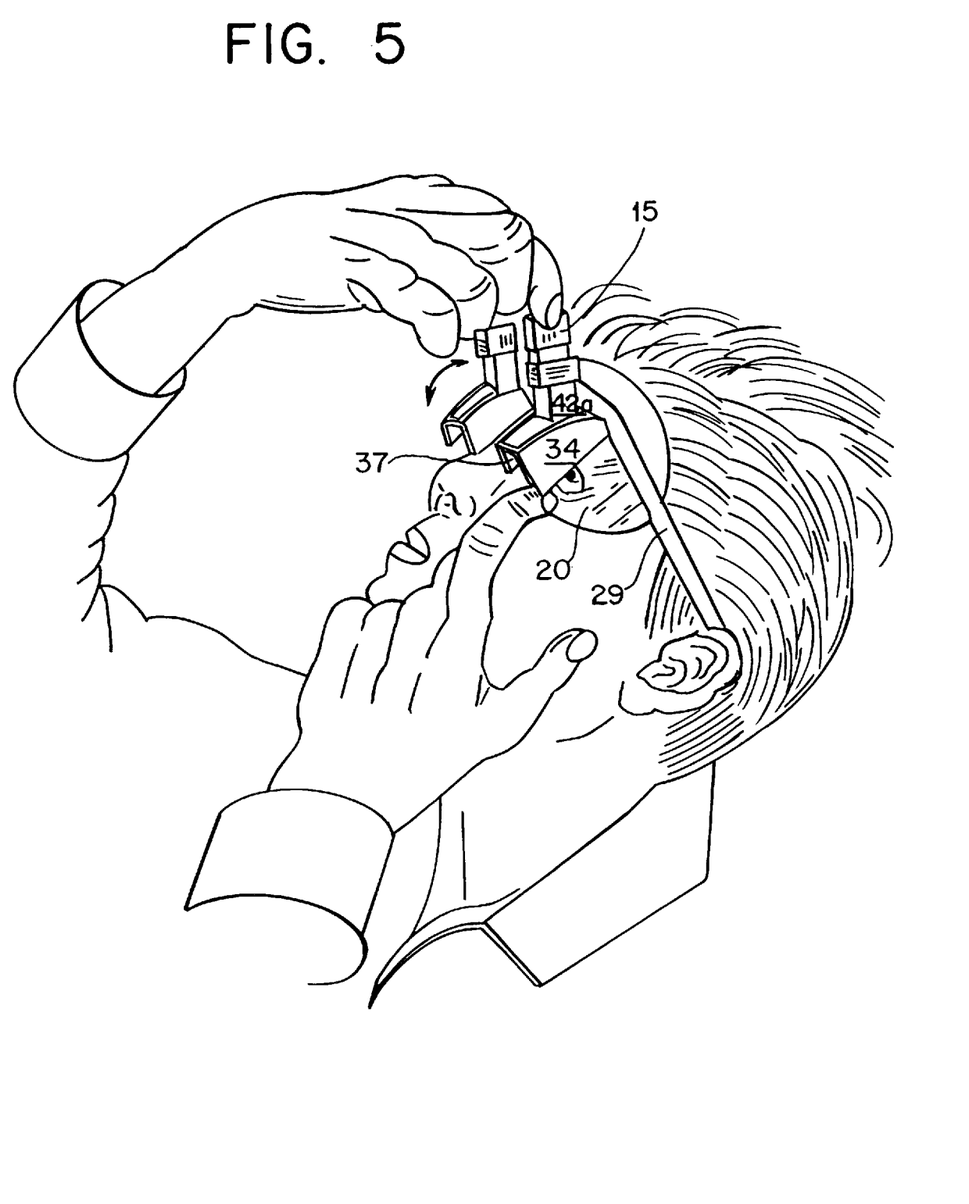
FIG. 5 is a perspective view of one embodiment of the present invention shown during eyedrop administration.

FIG. 5 shows the FIG. 1 embodiment of the present invention during administration. As can be appreciated from this particular figure, a patient can easily manipulate the lower portion of his/her eye or eyelid to expose the conjunctival sac which is typically considered to be the ideal area for administering eyedrop solution to the eye. When tip 17 of container 15 is attached to receiving port 45, device 10 is placed onto the head of a patient in the same manner as a typical pair of glasses. Ideally, device 10 is pushed back against the patient's forehead firmly into position on nose bridge 24. The patient then tilts his/her head back until the eyedrop container 15 is approximately vertical and using his/her finger exposes the lower portion of his/her eye or eyelid through lower opening 47 of eyedrop guide 30. The patient then adjusts container 15 (which in this particular embodiment is attached to the moveable port) over his/her eye and squeezes the same the prescribed number of times. Alternatively, the patient can adjust guide 30 prior to placing device 10 onto his/her head. Once an ideal eyedrop point is determined, the patient can mark this position on guide 30 along the arcuate path so as to repeatably insure successful administration. Advantageously, a guide lock (not shown) can also be incorporated on device 10 so that moveable container port 40 can be selectively secured at an individual patient's ideal drop position.

Figure 6:
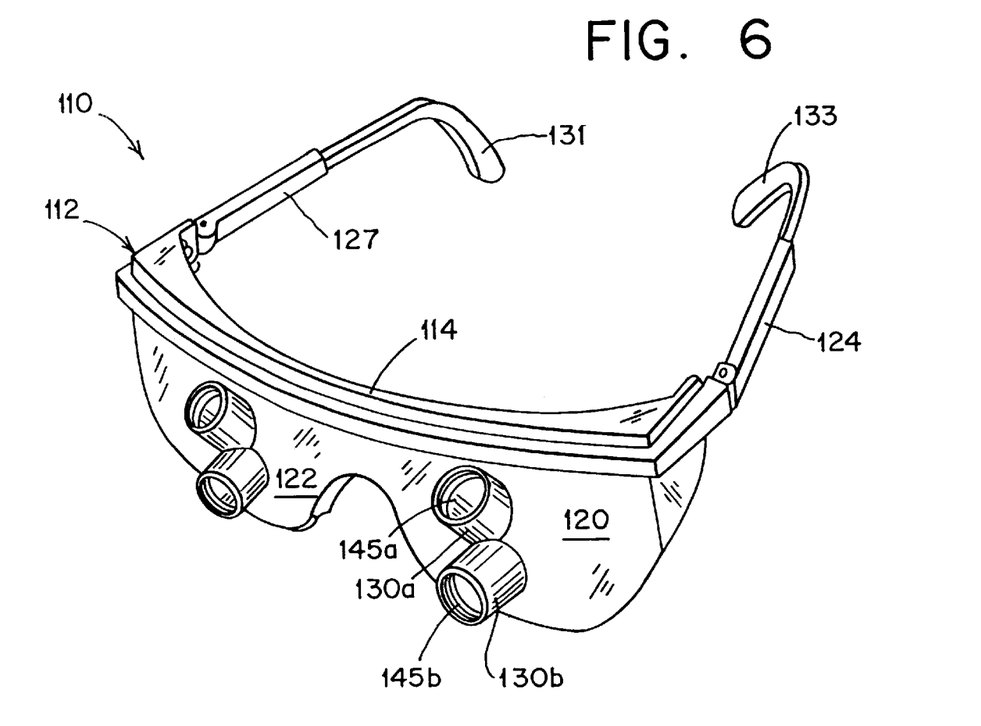
FIG. 6 is a perspective view of an alternative embodiment of the present invention.
Figure 7:
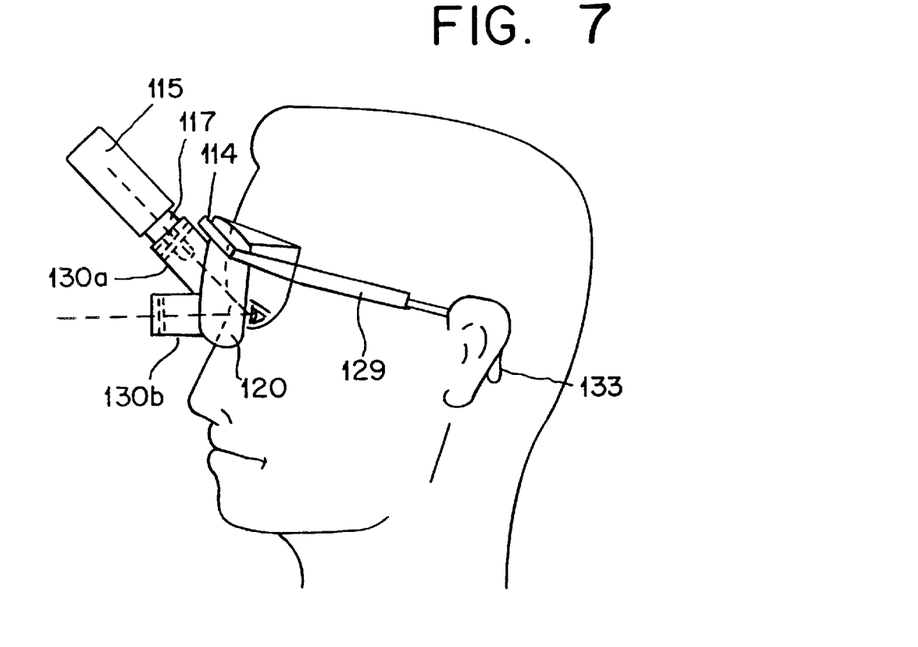
FIG. 7 is a side view of the alternative embodiment of FIG. positioned on a patient.

FIGS. 6 and 7 depict an alternative embodiment of the present invention 110 wherein the eyedrop guide has two fixed-position options—one option is used for administering an eyedrop while sitting and the other option is used for administering the eyedrop while in the prone position. This particular embodiment incorporates two receiving ports 145a and 145b on one or two guide(s) 130a and 130b, respectively. As can be appreciated from the present disclosure, this design can also incorporate many of the aforementioned features of the FIG. 1 embodiment, including, but not limited to the following: more than one eyedrop guide positioned on the eyeglass frame or within the eyeglass shield; thread-like, snap-fit or frictional engagement of the container 115; a laterally oriented slideable eyedrop guide track system disposed between shield 120 and 122 so that one eyedrop guide can alternatively be used to administer eyedrop solution to either eye; alternate means for securing device 10 to the head of a patient; and an eyedrop guide 130a and 130b which is dimensioned somewhat smaller than represented in FIG. 6 so that the guide 130a and 130b can moves along a vertically oriented track located within either one or both of the shields 120, 122 in some limited fashion.

Figures 8A, 8B, 8C:
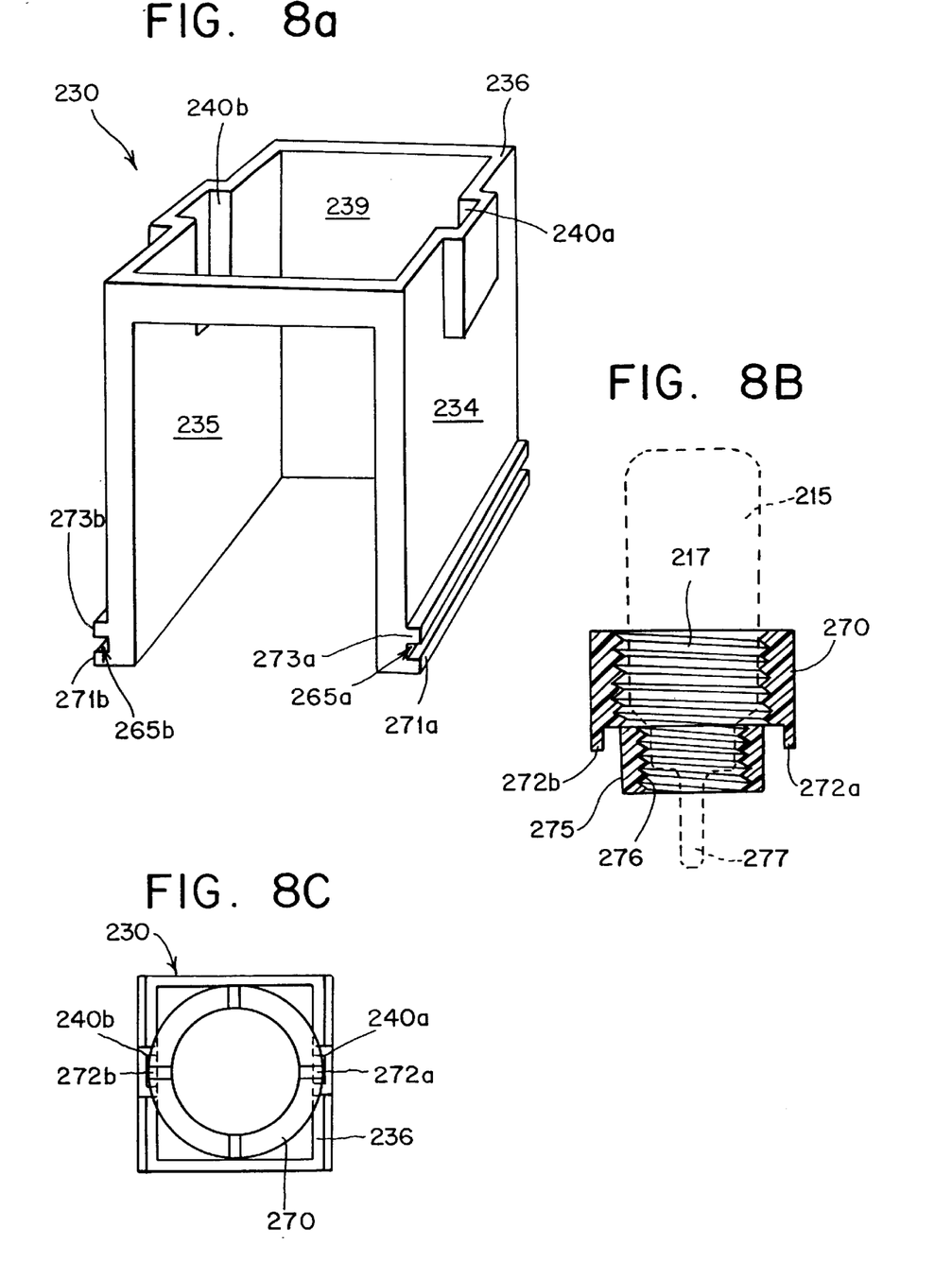
FIG. 8a is a perspective of an alternative embodiment of an eyedrop guide.
FIG. 8b is a cross section of a threaded sleeve with an eyedrop container engaged thereon.
FIG. 8c is a top view of the eyedrop guide of FIG. 8a gaged with the threaded sleeve.
Figure 8D:
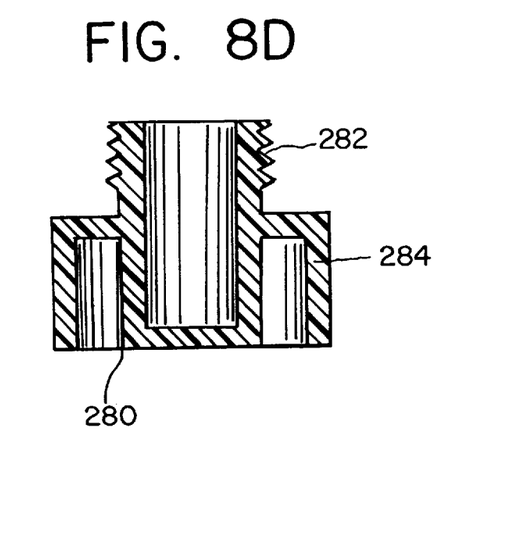
FIG. 8d is a cross section of the removable container cap.

FIGS. 8a–8d depict an alternative embodiment of the eyedrop guide wherein a threaded sleeve 270 is permanently attached to threaded top 217 of eyedrop container 215. In this particular embodiment, the frontal plate 236 of the guide 230 comprises two opposing slots 240a, 240b located on opposite sides thereof and threaded sleeve 260 comprises two opposing ribs 272a, 272b which depend therefrom and which are sized and dimensioned to generally reciprocate slots 240a, 240b, respectively (seen best in FIG. 8c). In order to secure the container 215 onto guide 230, ribs 272a, 272b are aligned with corresponding slots 240a, 240b and forced into frictional engagement with the same thus securing container 215 in place for administrative purposes. FIG. 8c shows a top view of threaded sleeve 270 engaged with guide 230 in the manner described above.

FIG. 8a shows guide 230 comprising two protruding guide rails or bars, 271a, 273a disposed on sidewall 234 and two protruding guide rails 271b, 273b disposed on sidewall 235. Rails 271a, 273a and 271b, 273b are generally arranged to run parallel to one another across each respective sidewall 234, 235 from bottom edges 243 to top portion 239, thus forming channels 265a and 265b, respectively, therein. Channel 265a and corresponding rails 271a, 273a and channel 265b and corresponding rails 271b, 273b are sized and dimensioned to engage or reciprocate a track or slot (not shown) located within shield portion 220 (or 222). In some cases it may be desirable to size guide 230 small enough so that guide 230 can move within the slot or track formed in the shield 220 (or 222).

In another embodiment, it may be desirable to size channels 265a, 265b (and rails 271a, 273a, and 271b, 273b) accordingly so that the they mutually cooperate with the eyedrop guide 30 of FIG. 4. As can be appreciated by the present disclosure, this would incorporate a three-piece device, i.e., guide 30, guide 230 and the container 215 and sleeve 260 combination. In this case, rails 271a, 273a, 271b, and 273b would be formed with a slight radius of curvature (thereby forming a corresponding channel with the same radius of curvature) which would correspond to the radius of curvature of channel edges 38a, 38b located in frontal plate 36 of FIG. 4. Channels 265a and 265b would reciprocate channel edges 38a and 38b respectively and guide 230 would thus be vertically adjustable along channel edges 38a, 38b. FIGS. 10a and 10b show this particular embodiment with an indicating mechanism attached to guide 230 which, as noted above, is movable along channel edges 38a, 38b of FIG. 4.

FIG. 8b shows a threaded sleeve 270 having a generally hollow internal threaded portion 275 which depends therefrom and which is sized and dimensioned to receive the extreme tip 277 of container 215. Container cap 280 (FIG. 8d) can be provided which is sized and dimensioned to engage the internal threads 276 of depending portion 275. As can be appreciated from the present disclosure, cap 280 allows a patient to seal container 215 when container 215 is engaged in guide 230 without having to disengage container 215 from guide 230. Cap 280 comprises external screws 282 which are dimensioned so as to engage internal threads 276 of depending portion 275. Cap 280 also comprises an outer rim portion 284 which allows a patient to securely grip cap 280 when sealing container 215.

It is not beyond the scope of this invention to provide cap 280 with an alternate means of attachment to extreme tip 277 of container 215. In addition, alternate designs for the frontal plate 236 include, but should not be limited to, resilient rubber-like protrusions or detents located within frontal plate 236 which grip container 215 and hold the same in place during administration.

Figure 9:
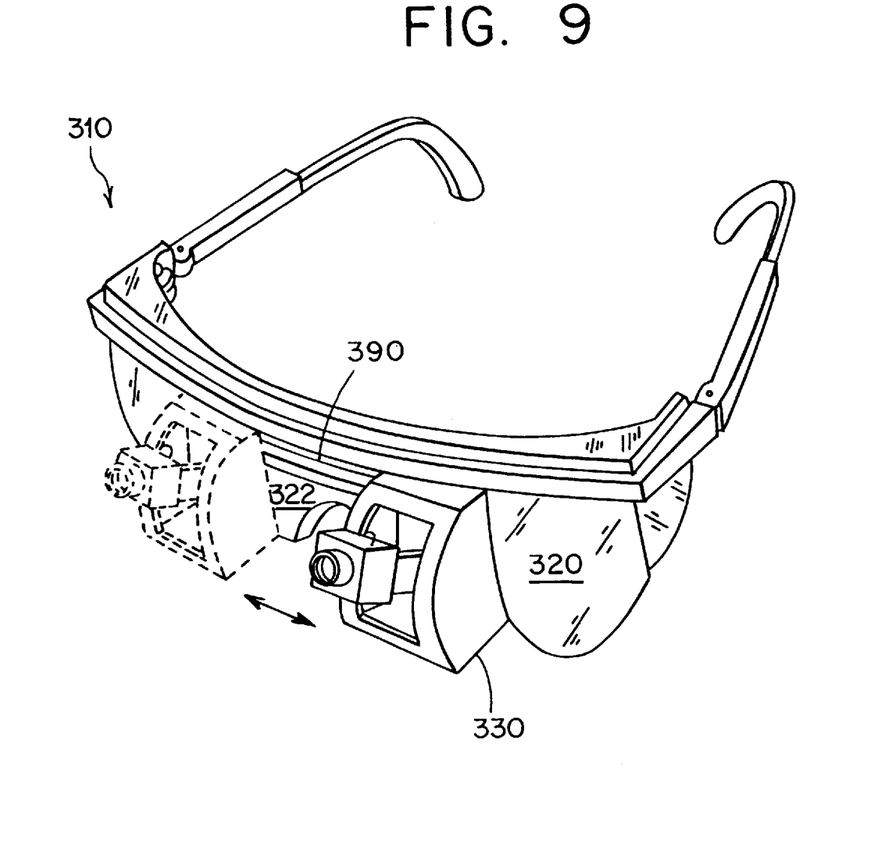
FIG. 9 is perspective view an alternative embodiment of the pesent invention.

FIG. 9 shows an alternative embodiment of the present invention wherein guide 330 is selectively moveable along track 390 which is located in shield 320, 322. As can be appreciated from the present disclosure, a patient can slide guide 330 from a position proximate the left eye to a position proximate the right eye or vice versa without having to disengage the eyedrop container (not shown). As can be appreciated, track 390 can be incorporated with various other embodiments of the present invention, e.g., the embodiment shown in FIGS. 6 and 7.

FIGS. 10a and 10b illustrates a gimbal device 291 and light source 297 configuration mounted to guide 230 by bar 293. Gimbal device 291 is rotatably mounted to bar 293 about swivel hinge 301 so that gimbal device 291 and light source 297 always remain in substantial vertical position. Fixed plate 295 is also affixed to guide 230 at a position closer to 271a, 273a or closer to the patient's eye. Fixed Plate 295 comprises a slit or small aperture 298 located therethrough for allowing light from light source 297 to permeate through slit 298 when guide 230 is substantially oriented in vertical position. As can be appreciated from the present disclosure, when patient readies himself/herself for eyedrop administration and is attempting to tilt back his/her head to a substantially vertical position, the light from the gimbal device 291 and light source 297 configuration will only permeate slit 298 when the patient has moved his/her head so that container 215 is substantially vertical, i.e., the light permeating slit 298 signals the patient to begin administering the eyedrops from container 215. Although FIG. 10a and 10b show fixed plate 295 and the gimbal device 291 and light source 297 configuration attached to sidewall 234 of eyedrop guide 230, it is not beyond the scope of this invention to position these components on sidewall 235 or perhaps another portion of device 10.

Various modifications may be made without departing from the scope of the present invention. For example, while the most of the component parts of the present invention are generally made from a plastic material, it may be desirable to construct one or more of the components from a different material such as aluminum or graphite. As described above, both embodiments of the present invention show eyedrop container 15 (or 215) attached via threads provided at the top of each attachment port. The majority of eyedrop containers currently sold in the U.S. have standard threaded top portions, however, it is not beyond the scope of the present invention to provide alternate means of attachment for containers 15 (or 215) which have larger threads such as over-the-counter eyedrop solutions. As noted above, the eyedrop guide 30 (230) can be equipped with a moveable container port 40 which is engagable with frontal plate 42 of eyedrop guide 30 (e.g., the notch and channel configuration described above) and also equipped with a different type of engagement mechanism for attaching virtually any type of eyedrop container 15 (or 215).

It may also be possible to combine both of the embodiments shown in FIG. 1 and FIG. 6 so that either eyedrop guide configuration can be selectively incorporated with an eyeglass frame depending upon a patient's particular preference.

I claim:

1. A device for administering eyedrops from an eyedrop container to an eye of a patient, comprising:
    at least one eyedrop guide, said eyedrop guide selectively slidable along a substantially arcuate path proximate an eye;
    means for attaching said eyedrop container to said eyedrop guide, wherein said attaching means is connected to said eyedrop guide; and
    means for selectively positioning said eyedrop guide proximate the patient's eye, wherein said eyedrop guide is slidably connected to said positioning means.

2. A device according to claim 1 wherein said positioning means further comprises an eyeglass-type frame comprising a bridge portion.

3. A device according to claim 2 wherein said guide is selectively positionable between a first position located a first distance from said bridge portion to at least one second position located closer to said bridge portion.

4. A device according to claim 3 further comprising:
    a shield portion connected to said bridge portion, said shield portion sized and dimensioned to substantially cover at least one eye of said patient; and
    wherein said eyedrop guide is attached to said shield portion.

5. A device according to claim 4 wherein said shield portion substantially covers both eyes of said patient and said eyedrop guide is selectively moveable across said shield portion from a first position generally located above the right eye of said patient to a second position generally located above the left eye of the patient.

6. A device according to claim 2 comprising a right eyedrop guide and a left eyedrop guide.

7. A device according to claim 1 wherein said attaching means comprises threads.

8. A device according to claim 3 wherein said positioning means comprises two temple portions rearwardly extending from said bridge portion, said temple portions each comprising a depending portion designed and dimensioned to generally extend around a portion of said patient's ear in a close-fit manner thereby holding said frame in a secure position.

9. A device according to claim 3 wherein said eyedrop guide comprises at least two portions, wherein said first portion is integral with said frame and said second portion engages said first portion in a snap-fit manner and wherein said second portion of said eyedrop guide is selectively moveable between said first position and said at least one second position.

10. A device according to claim 9 wherein one of said portions further comprises means for selectively positioning said container at a plurality of positions along said substantially arcuate path.

11. A device according to claim 9 wherein said eyedrop guide further comprises:
    two resilient flanges depending from said second portion, at least one of said flanges comprising a means for attaching at least one of said flanges to said portion.

12. A device according to claim 11 wherein said attaching means comprises a notch.

13. A device according to claim 11 wherein said attaching means comprises at least one of said flanges comprising at least one notch and wherein said first portion comprises at least one guide bar located thereon generally dimensioned to receive said notch and generally positioned to run parallel along said substantially arcuate path such that when said second portion is engaged with said first portion, said second portion is selectively positionable along said substantially arcuate path.

14. A device according to claim 1 further comprising a cap for sealing the eyedrop container when engaged with said at least one eyedrop guide.

15. A device for administering eyedrops from an eyedrop container to an eye of a patient, comprising:
    at least one eyedrop guide, said eyedrop guide comprising a lower portion having a recess which is dimensioned to permit said patient to manipulate the lower portion of said patient's eye with said patient's finger prior to administering said eyedrop;
    means for attaching said eyedrop container to said eyedrop guide, wherein said attaching means is connected to said eyedrop guide; and
    means for selectively securing said eyedrop guide proximate the patient's eye, wherein said eyedrop guide is slidably connected to said positioning means.

16. A device according to claim 15 wherein said eyedrop guide further comprises at least three walls which define an inner cavity located within said guide, said cavity dimensioned to permit said patient to manipulate the lower portion of said patient's eye with said patient's finger prior to administering said eyedrop.

17. A device according to claim 16 wherein said eyedrop guide comprises two sidewalls, a top portion and a frontal plate which define said cavity.

18. A device according to claim 15 further comprising an eyeglass-type frame comprising an upper bridge portion.

19. A device according to claim 18 wherein said guide is positionable between a first position located a first distance from said bridge portion to at least one second position located closer distance to said bridge portion.

20. A device according to claim 19 further comprising:
    an shield portion connected to said bridge portion, said shield portion sized and dimensioned to substantially cover at least one eye of said patient; and
    wherein said eyedrop guide is attached to said shield portion.

21. A device according to claim 19 comprising a right eyedrop guide and a left eyedrop guide.

22. A device according to claim 18 wherein said attaching means comprises threads.

23. A device according to claim 20 wherein said eyedrop guide comprises at least two portions, wherein said first portion is integral with said frame and said second portion is selectively engagable with said first portion.

24. A device according to claim 23 wherein said eyedrop guide further comprises:
    two resilient flanges depending from said second portion, at least one of said flanges comprising a means for attaching at least one of said flanges to said portion.

25. A device according to claim 18 further comprising a cap for sealing the eyedrop container when engaged with at least one eyedrop guide.

26. A device for administering eyedrops from an eyedrop container to an eye of a patient, comprising:
    at least one eyedrop guide, said eyedrop guide selectively slidable along a substantially arcuate path proximate an eye;
    means for attaching said eyedrop container to said eyedrop guide, wherein said attaching means is connected to said eyedrop guide;

means for selectively positioning said guide proximate the patient's eye, wherein said eyedrop guide is slidably connected to said positioning means; and means for indicating when said eyedrop container is positioned over the eye for administration.

27. A device according to claim 26 further comprising an eyeglass-type frame comprising an upper bridge portion.

28. A device according to claim 27 wherein said guide is positionable between a first position located a fixed distance from said bridge portion to at least one second position located closer to said bridge portion.

29. A device according to claim 26 wherein said indicating means comprises a level indicator.

30. A device according to claim 26 wherein said level indicator is attached to said eyedrop guide.

31. A device according to claim 26 wherein said indicating means comprises a light.

32. A device according to claim 26 wherein said indicating means comprises an audible alarm.

* * * * *